(12) United States Patent
Haitsuka (10) Patent No.: US 10,265,472 B2
(45) Date of Patent: Apr. 23, 2019

(54) INJECTOR

(71) Applicant: DAICEL CORPORATION, Osaka (JP)

(72) Inventor: Masahiro Haitsuka, Hyogo (JP)

(73) Assignee: Daicel Corporation, Osaka (JP)

( * ) Notice: Subject to any disclaimer, the term of this patent is extended or adjusted under 35 U.S.C. 154(b) by 0 days.

(21) Appl. No.: 14/897,373

(22) PCT Filed: Jun. 12, 2014

(86) PCT No.: PCT/JP2014/065616
§ 371 (c)(1),
(2) Date: Dec. 10, 2015

(87) PCT Pub. No.: WO2014/200066
PCT Pub. Date: Dec. 18, 2014

(65) Prior Publication Data
US 2016/0129190 A1 May 12, 2016

(30) Foreign Application Priority Data

Jun. 12, 2013 (JP) .................................. 2013-123702

(51) Int. Cl.
*A61M 5/20* (2006.01)
*A61M 5/24* (2006.01)
*A61M 5/30* (2006.01)

(52) U.S. Cl.
CPC ............ *A61M 5/2046* (2013.01); *A61M 5/24* (2013.01); *A61M 5/30* (2013.01); *A61M 2005/2414* (2013.01)

(58) Field of Classification Search
CPC ........ A61M 5/2046; A61M 5/24; A61M 5/30; A61M 2005/2414; A61M 2005/2418
(Continued)

(56) References Cited

U.S. PATENT DOCUMENTS 4,089,334 A * 5/1978 Schwebel ............... A61M 5/30
604/143
5,080,648 A 1/1992 D'Antonio
(Continued)

FOREIGN PATENT DOCUMENTS

CA 2742555 A1 12/2012
DE 10215297 A1 10/2003
(Continued)

OTHER PUBLICATIONS dictionary.com definition of plastic, pdf dated Dec. 10, 2016.*
(Continued)

*Primary Examiner* — Nathan R Price
*Assistant Examiner* — John A Doubrava
(74) *Attorney, Agent, or Firm* — Knobbe Martens Olson & Bear LLP (57) ABSTRACT

An injector includes a syringe unit including a syringe that encapsulates an injection objective substance, an ignition device, and a piston, and an activating unit that activates the syringe unit. The syringe unit includes a cylindrical housing, in which the ignition device and the piston are incorporated, and can be installed in a housing space formed in the housing through an opening section provided in a side surface of the housing. The syringe includes a nozzle and a plunger that forms a sealed space for encapsulating the injection objective substance and that is capable of being propelled toward the nozzle by the piston. When the syringe is installed in the housing, the syringe is fixed to dispose the plunger of the syringe in a position opposed to the piston incorporated in the housing.

13 Claims, 7 Drawing Sheets

(58) Field of Classification Search
USPC .......................................................... 604/147
See application file for complete search history.

(56) References Cited

U.S. PATENT DOCUMENTS

| | | | |
|---|---|---|---|
| 6,045,534 A | 4/2000 | Jacobsen et al. | |
| 6,056,716 A * | 5/2000 | D'Antonio | A61M 5/24 |
| | | | 604/134 |
| 6,090,082 A | 7/2000 | King et al. | |
| 6,258,063 B1 | 7/2001 | Haar et al. | |
| 7,261,702 B1 | 8/2007 | Alexandre et al. | |
| 2003/0050596 A1 | 3/2003 | Alexandre et al. | |
| 2003/0105430 A1 | 6/2003 | Lavi et al. | |
| 2003/0114789 A1 | 6/2003 | Haar et al. | |
| 2003/0149396 A1 * | 8/2003 | Alexandre | A61M 5/30 |
| | | | 604/68 |
| 2003/0173110 A1 * | 9/2003 | Gross | A61M 5/178 |
| | | | 174/260 |
| 2005/0010167 A1 | 1/2005 | Alexandre et al. | |
| 2006/0258986 A1 | 11/2006 | Hunter et al. | |
| 2006/0281175 A1 | 12/2006 | McSwiggen et al. | |
| 2007/0079777 A1 | 4/2007 | Hurlstone et al. | |
| 2007/0191758 A1 | 8/2007 | Hunter et al. | |
| 2008/0009788 A1 | 1/2008 | Hunter et al. | |
| 2008/0088144 A1 * | 4/2008 | Crown | A45F 5/10 |
| | | | 294/146 |
| 2010/0076375 A1 * | 3/2010 | Alexandre | A61M 5/30 |
| | | | 604/69 |
| 2011/0257626 A1 | 10/2011 | Hunter et al. | |
| 2013/0102957 A1 | 4/2013 | Hunter et al. | |
| 2015/0005701 A1 | 1/2015 | Hunter et al. | |
| 2016/0197542 A1 | 7/2016 | Hunter et al. | |

FOREIGN PATENT DOCUMENTS

| | | |
|---|---|---|
| EP | 1570875 A1 | 9/2005 |
| EP | 2468341 A1 | 6/2012 |
| JP | H06-328195 A | 11/1994 |
| JP | H07-257306 A | 10/1995 |
| JP | 2003-518960 A | 6/2003 |
| JP | 2003-194261 A | 7/2003 |
| JP | 2003-530147 A | 10/2003 |
| JP | 2005-511254 A | 4/2005 |
| JP | 2005-523679 | 8/2005 |
| JP | 2007-525192 A | 9/2007 |
| JP | 2008-508881 A | 3/2008 |
| JP | 2008-529677 A | 8/2008 |
| JP | 2008-206477 A | 9/2008 |
| JP | 2010-503616 | 2/2010 |
| JP | 2013-094344 A | 5/2013 |
| WO | WO 99/21609 | 5/1999 |
| WO | WO 01/05451 A1 | 1/2001 |
| WO | WO 2004/093948 A1 | 11/2004 |
| WO | WO 2012/032411 A2 | 3/2012 |

OTHER PUBLICATIONS

Extended European Search Report, dated Apr. 28, 2016, received in corresponding European Patent Application No. 14811178.4.
International Search Report for International Application No. PCT/JP2014/065616, dated Sep. 16, 2014.
International Preliminary Report on Patentability, dated Dec. 23, 2015, issued in corresponding International Patent Application No. PCT/JP2014/065616.
Office Action dated Nov. 8, 2016 in corresponding Japanese Patent Application No. 2013-123702.
Search Report dated Oct. 24, 2016 in the corresponding Singapore Patent Application No. 11201510215V.
Office Action dated Sep. 5, 2017 in corresponding Japanese Application No. 2013-123702.
Office Action dated Apr. 24, 2018 in related Chinese Application No. 201480044724.4.

* cited by examiner

INJECTOR

CROSS-REFERENCE TO RELATED APPLICATIONS

This application is the U.S. National Phase under 35 U.S.C. § 371 of International Application PCT/JP2014/065616, filed Jun. 12, 2014, which claims priority to JP 2013-123702, filed Jun. 12, 2013.

TECHNICAL FIELD

The present invention relates to an injector for injecting an injection objective substance into an injection target region.

BACKGROUND ART

An injector includes a syringe in which an injection component (an injection objective substance) is encapsulated. The injector drives a piston with respect to the injection component to eject the injection component. There is an injector that supplies, with, for example, pressure by a pressurized gas, a spring, combustion by an explosive component or the like, force for driving the piston.

For example, an injector disclosed in Patent Literature 1 is an injector actuated by a propellant. An internal shell and a chemical unit are incorporated in a main body. The propellant is disposed in the internal shell and stored in an external shell together with the chemical unit. The external shell is fit in the main body and covered with a cover. Chemical is ejected by combustion of the propellant. An injector disclosed in Patent Literature 2 is an injector of a handgun type. A part (the peripheral surface) of a main body is opened. A cartridge is inserted from this opening section. The cartridge includes a piston, a bellows section, in which chemical is stored, and a nozzle. In the injector, the chemical is ejected by the force of a spring.

CITATION LIST

Patent Literature

[PTL 1] U.S. Pat. No. 6,258,063
[PTL 2] U.S. Pat. No. 5,080,618

SUMMARY OF INVENTION

Technical Problem

In an injector, since an injection component is included in a syringe, the syringe needs to be kept sterile until immediately before injection. In particular, when an injection objective substance is injected only once, the injector touches skin (an injection target) once. Therefore, the reproduction of bacteria and the like can be avoided. But, when the syringe is replaced and used every time the injection is performed, a sanitation problem concerning contamination of a replaced new syringe has to be sufficiently taken into account.

When pressure generated by combustion of an explosive component or the like is used as a driving source of a piston in the injector, since it is easy to adjust the pressure applied to the piston, the pressure is considered to be a useful driving source. However, the residue to the explosive component or the like occurs when the explosive component or the like is burned. Therefore, component once used is desirably discarded. At this point, a residue component desirably does not leak out to the outside from the viewpoint of sanitation (a place which a hand of a user reaches) to prevent the hand of the user from being stained, when components after use are removed or detached.

However, in the injector of Patent Literature 1 described above, the chemical unit comes off the internal shell at the moment that the external shell is taken out from the housing after use. Therefore, it is likely that a combustion residue adheres to the hand. In particular, since the external shell is inserted into the main body and used, the main body is used a plurality of times. It is conceivable that the main body is affected by the residue every time the use is repeated. In the injector of Patent Literature 2 described above, although the driving source is not limited to the explosive component and the like, the injector includes a configuration for repeatedly loading the cartridge in the inside. Therefore, when bacteria adhering after the injection and an injection solution leaked during the injection adhere to the main body (e.g., the piston), problems of sanitation influence arise when a new cartridge is installed.

Therefore, the present invention has been devised in view of the problem and it is an object of the present invention to provide an injector that, although including a structure for replacing a syringe including an injection objective substance every time injection is performed, even if the injection objective substance leaked during the injection adheres to the syringe, can prevent the influence of the injection objective substance from reaching the next new syringe and prevent the influence of a combustion residue of an explosive component used as a driving source from reaching the new syringe.

Solution to Problem

In order to solve the problems, the inventors directed attention, in particular, to a syringe unit configuring an injector. Specifically, the present invention is an injector including: a syringe unit including a syringe that encapsulates an injection objective substance to be injected into an injection target region, an ignition device that gives, by combustion of an explosive component, energy for ejection to the injection objective substance encapsulated in the syringe, and a piston disposed between the syringe and the ignition device and capable of transmitting the energy given by the ignition device to the syringe side; and an activating unit that activates the ignition device included in the syringe unit. The syringe unit includes a cylindrical housing in which the ignition device and the piston are incorporated. The syringe can be installed in a housing space formed in the housing through an opening section provided in a side surface of the housing. Further, the syringe includes a nozzle formed at a distal end portion of the syringe and for injecting the injection objective substance to the injection target region and a plunger disposed in a proximal end portion on a side opposite to the distal end portion, a sealed space for encapsulating the injection objective substance being formed by the plunger and an inner wall of the syringe, and the plunger being capable of being propelled, toward the nozzle, on the inside of the syringe by energy transmitted from the piston. When the syringe is accommodated in the housing, the syringe is fixed to dispose the plunger of the syringe in a position opposed to the piston incorporated in the housing.

The injector according to the present invention uses the explosive component as a driving source for ejection of the injection objective substance. As the ignition device, only a publicly-known electric igniter including an explosive component such as ZPP (a mixture of zirconium and potassium perchlorate) may be used or publicly-known black powder (boron saltpeter) or a publicly-known gas generating agent (e.g., cellulose nitrate-based) can be used together with the electric igniter.

In the injector according to the present invention, the injection objective substance is encapsulated in the syringe, at the distal end portion of which the nozzle is formed. The nozzle may be formed integrally with the syringe or may be attached to the syringe as another member. In the syringe, the plunger is provided at the proximal end portion on the opposite side in the axial direction of the distal end portion where the nozzle is formed. The sealed space, in which the injection objective substance is encapsulated, is formed by the plunger and the inner wall of the syringe. The plunger is disposed on the inside of the syringe, that is, the sealed space to be capable of being propelled toward the nozzle. Note that, as explained below, energy generated by the ignition device is transmitted to the plunger via the piston, whereby the plunger performs propulsion in the sealed space.

The syringe can be installed in the housing of the syringe unit in which the ignition device and the piston are incorporated. That is, the ignition device and the piston are incorporated in the housing in advance. However, concerning the syringe, any syringe selectable by the user according to necessity such as a predetermined syringe in which a desired injection objective substance corresponding to an injection purpose is encapsulated or a predetermined syringe having a nozzle diameter suitable for the injection target region is selectively installed in the housing, whereby the injector is configured. For installing the syringe in the housing, the opening section is provided on the side surface of the cylindrical housing. Note that the opening section does not always need to have size same as the sectional shape of the syringe and only has to have size enough for attaching the syringe to the housing.

The plunger present at the distal end portion of the syringe is disposed to be opposed to the piston incorporated in the housing when the syringe is installed in and fixed to the housing via the opening section. As the fixing of the syringe to the housing, it is possible to use publicly-known fixing methods such as a method of pressing the proximal end portion of the syringe to the piston side using an elastic body or the like, a method of bringing the syringe into contact with or fitting the syringe in a protrusion formed on the inside of the housing, a method of fixing the syringe to the housing using a predetermined member for fixing, and a method by an adhesive tape. Note that the fixing of the syringe to the housing is not limited to the fixing methods indicated above as long as the syringe is properly fit without backlash when being installed in the housing and the syringe is held in the housing such that the piston can smoothly push the plunger.

The syringe unit is connected to the activating unit. The ignition device incorporated in the syringe unit receives supply of electric power for activation by the activating unit. For example, if the ignition device is an ignition device in which an electric igniter is used, a circuit and a battery for supplying an ignition current to the igniter, an actuation switch, a diagnostic device for the circuit, and the like are disposed in the activating unit. When the injection objective substance is ejected, the user can grip the activating unit and operate the injector. Note that various forms can be adopted as a form of the connection of the syringe unit and the activating unit. For example, the units may be formed by individual containers (housings). The syringe unit may be attached and fixed to the outer peripheral section of the container on the activating unit side and receive power supply. The syringe unit and the activating unit may be connected in a form in which the syringe unit is housed on the inside of an outer container configuring the activating unit. The syringe unit may receive power supply from the activating unit side.

In the injector configured in this way, after the injection objective substance is emitted by operation of the ignition device, the syringe unit is removed from the activating unit and discarded. The syringe unit after use includes the ignition device, the syringe, and the piston as explained above. The syringe is fixed to the syringe unit on the inside. Therefore, a residue less easily leaks to the outside of the syringe unit during the operation and after the operation. Even if the injection objective substance leaks into the syringe unit, since the syringe unit is replaced in whole, it is extremely less likely that the hand of the user operating the injector is contaminated by the residue and the injection objective substance. That is, in the present invention, the syringe unit is discarded after being used once. It is possible to eliminate, as much as possible, likelihood that the syringe unit contaminates a new syringe and a new syringe unit installed in the next new injector.

Before election of the injection objective substance, the syringe unit of the present invention is desirably stored in a sealed container or the like while being divided into the syringe and the syringe unit not installed with the syringe, that is, the housing in which the ignition device and the piston are incorporated. Immediately before the use, the sealing of the syringe and the syringe unit is released and the syringe is housed in the housing from the opening section. At this point, unlike the Patent Literature 1 described above, complicated work for installing the internal shell having the propellant and the injection solution unit in the external shell together is unnecessary. That is, since the ignition device is incorporated in advance in the housing used in the present invention, the syringe unit is completed if only the syringe is incorporated in the housing at a point of use. Therefore, the user does not need to touch unnecessary components. The syringe is installed from a side surface of the housing. Therefore, assembly of the syringe unit is also simple. Note that it is desirable in terms of sanitation as well to separately seal the syringe and the housing. However, at a stage before use, the housing does not always have to be sealed and stored. Only the syringe, in which the injection objective substance is encapsulated, may be sealed and stored.

In the injector, the ignition device may be formed to be integrated with the housing. In this way, it is easy to manage the housing before use. In particular, since the explosive component is used in the ignition device, by integrating the ignition device with the housing, it is possible to suppress the user from carelessly accessing the explosive component in the ignition device. More specifically, when the housing is formed by injection molding of a resin material, the ignition device may be integrated with the housing in a state in which the ignition device is embedded in the housing during the injection molding of the housing. The housing and the ignition device are integrated by a method of so-called insert molding.

When the ignition device and the housing made of resin are integrally molded in this way, it is likely that the housing is damaged by heat generated in the ignition device. Therefore, to reduce the thermal damage to the housing, in the injector, in the housing, heat-resistant members may be provided between the ignition device and the resin material of the housing and between the piston and the resin material of the housing to cover at least parts of the ignition device and the piston disposed in the housing. The heat-resistant members are members that are not deformed by heat when the ignition device operates and burns and strength of which is not deteriorated. For example, metal, ceramic, and the like can be used. These heat-resistant members are desirably disposed to surround the entire ignition device and surround the entire piston in order to obtain a reducing effect for the thermal damage as much as possible. Further, the ignition device and the piston may be surrounded by an integrally formed heat-resistant member. By disposing such a heat-resistant member, deformation of the housing made of resin due to heat after the operation of the ignition device is suppressed to make it easy to replace the syringe unit.

In the injector, since the diameter of the nozzle is relatively small compared with the diameter of the syringe main body, a relatively large load tends to be applied to the wall surface of the syringe when a load is applied to the syringe from the piston during the operation. Therefore, it is likely that the syringe is deformed or broken. Therefore, in the housing, a reinforcing member may be provided between the syringe and the housing to cover at least a part of the syringe installed in the housing. If the reinforcing member is disposed to cover the syringe in this way, it is possible to avoid the deformation and the breakage even if the load is applied to the syringe wall surface.

In the injector explained above, a lid section capable of opening and closing the opening section may be provided in the housing. Although the syringe is fixed to the housing, since the lid section is provided in the housing, it is possible to prevent drop of the syringe by any chance. Note that the lid section may be a lid section that is completely detached from the housing or may be a lid section that is connected to the housing in a part and can be opened and closed in a door shape. The lid section may be formed of a material same as the material of the housing or may be formed of a different material.

In the injector explained above, in a state in which the syringe is installed in the housing, the nozzle of the syringe may be exposed from the housing. For example, in a case where the housing has a through-hole, which connects the inside and the outside of the housing, in a distal end face of an end portion of the housing space, with the end portion being on a side opposite to the ignition device, when the syringe is installed in the housing, the syringe may be fixed to the housing in a state in which the syringe is held in the through-hole and may be configured such that the nozzle is exposed from the through-hole. By configuring the syringe in this way, it is possible to facilitate positioning of the syringe with respect to the housing. The user can complete ejection preparation of the injection objective substance with simple operation.

Advantageous Effects of Invention

It is possible to provide an injector that, although including a structure for replacing a syringe including an injection objective substance every time injection is performed, even if the injection objective substance leaked during the injection adheres to the syringe, can prevent the influence of the injection objective substance from reaching the next new syringe and prevent the influence of a combustion residue of an explosive component used as a driving source from reaching the new syringe.

DESCRIPTION OF EMBODIMENTS

A needleless injector 1 (hereinafter simply referred to as "injector 1") according to an embodiment of the present invention is explained below with reference to the drawings. Note that a configuration of the embodiment explained below is illustration. The present invention is not limited to the configuration of the embodiment.

<Configuration of the Injector 1>

Figure 1:
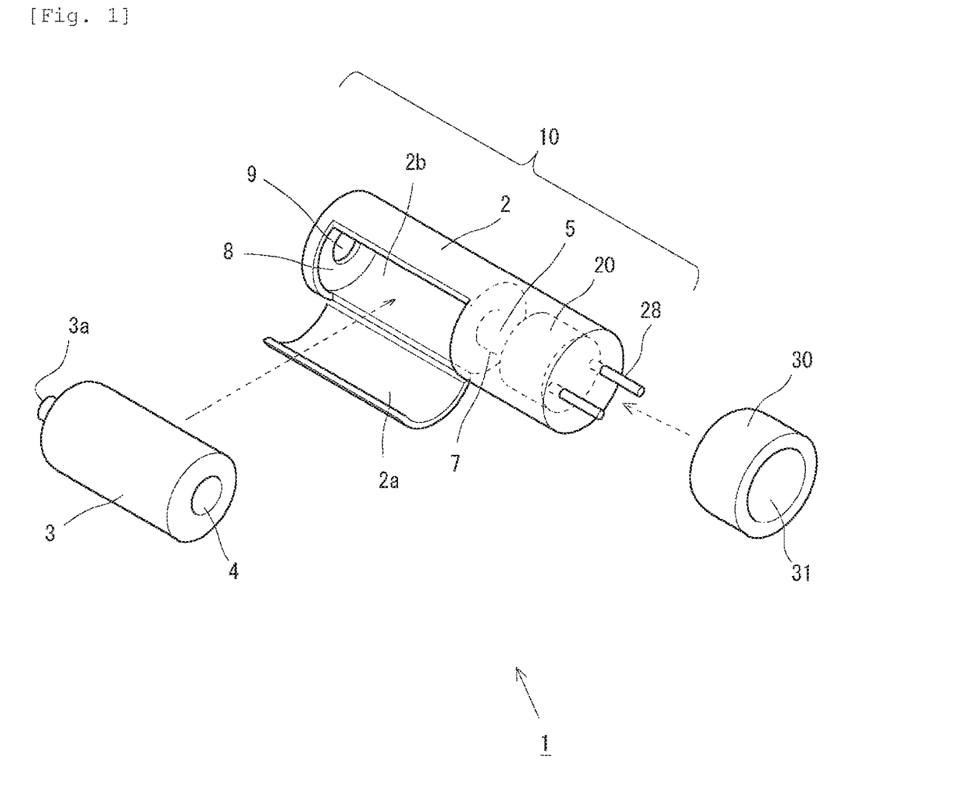
FIG. 1 is a first diagram showing the schematic configuration of an injector according to the present invention.

FIG. 1 is a perspective view of the injector 1. Note that the injector 1 shown in FIG. 1 is configured by a syringe unit 10 and an activating unit 30 explained below. However, FIG. 1 simply shows the concept of the invention and does not show relative sizes of the units. In the following description of this application, an injection objective substance injected into an injection target region by the injector 1 is generally referred to as "injection solution". However, this does not intend to limit contents and forms of substances to be injected. In the injection objective substance, a component that should be delivered to a skin structure or the like, which is the injection target region, may be dissolved or may not be dissolved. A specific form of the injection objective substance may be any form as long as the injection objective substance can be ejected to the injection target region from a nozzle 3a by being pressurized. Various forms such as liquid and gel forms can be adopted.

The injector 1 is configured from the syringe unit 10 and the activating unit 30. The syringe unit 10 is a unit that is thrown away every time ejection of the injection solution is performed. On the other hand, the activating unit 30 is a unit that can be repeatedly used as long as electric power of a battery incorporated therein remains.

Figure 5:
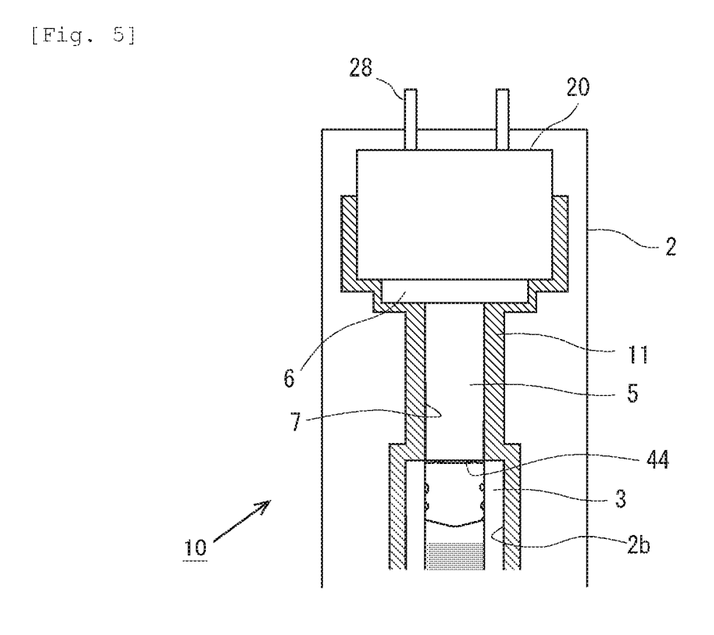
FIG. 5 is a sectional view of a syringe unit included in the injector shown in FIG. 1.

First, the syringe unit 10 is explained with reference to FIG. 1 and FIG. 5. Note that FIG. 5 is a sectional view of the syringe unit 10. The syringe unit 10 includes a housing 2 formed in a cylindrical shape. In the housing 2, an initiator 20, which is an electric igniter that burns an explosive component to generate energy for election, and a piston 5, which transmits the energy generated by the initiator 20 to a syringe 3 side explained below, are incorporated. Specifically, the housing 2 is manufactured by injection molding of resin. Concerning the injection molding, a publicly-known method can be used. When the housing 2 is manufactured, the initiator 20 is insert-molded to be integrated with the housing 2 in a form in which a charge holder 23 side explained below are exposed. As a resin material of the housing 2, for example, publicly-known nylon 6-12, polyarylate, polybutylene terephthalate, polyphenylene sulfide, or liquid crystal polymer can be used. A filler such as a glass fiber or a glass filler may be included in these kinds of resin. 20 to 80 mass % of the glass fiber can be included in the polybutylene terephthalate. 20 to 80 mass % of the glass fiber can be included in the polyphenylene sulfide, 20 to 80 mass % of mineral can be included in the liquid crystal polymer.

Figure 2:
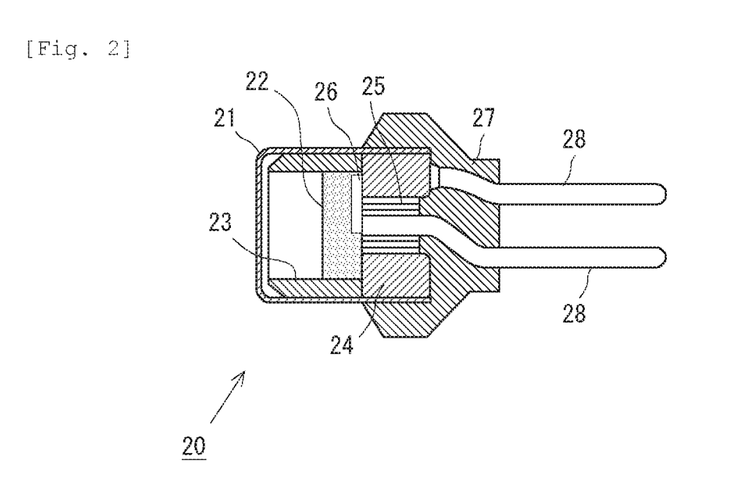
FIG. 2 is a diagram showing the configuration of an initiator included in the injector shown in FIG. 1.

An example of the initiator 20 is explained with reference to FIG. 2. The initiator 20 is an electric igniter. A cup 21, the surface of which is covered with an insulating cover, defines, in the cup 21, a space for disposing an ignition charge 22. A metal header 24 is disposed in the space. A cylindrical charge holder 23 is provided on the upper surface of the metal header 24. The ignition charge 22 is held by the charge holder 23. A bridge wire 26, which electrically connects one of conductive pins 28 and the metal header 24, is wired in the bottom of the ignition charge 22. Note that two conductive pins 28 are fixed to the metal header 24 via an insulator 25 to be insulated from each other. Further, an opening of the cup 21, from which the two conductive pins 28 supported by the insulator 25 extend, is protected in a state in which insulation between the conductive pins 28 is satisfactorily maintained by resin 27.

In the initiator 20 configured in this way, an electric current flows to the bridge wire 26 when a voltage is applied between the two conductive pins 28 by an external power supply. Consequently, the ignition charge 22 burns. At this point, a combustion product by the combustion of the ignition charge 22 is ejected from an opening section of the charge holder 23 while breaking the cup 21. Therefore, in the present invention, a combustion chamber 6 having a predetermined capacity is disposed in front of the charge holder 23 (a direction opposite to a direction in which the conductive pins 28 extend) such that the combustion product of the ignition charge 22 in the initiator 20 flows into the combustion chamber 6. Note that, since the initiator 20 is formed integrally with the housing 2 as explained above, at is unlikely that the initiator 20 itself comes off the housing 2 with pressure generated during ignition in the initiator 20.

Note that examples of the ignition charge 22 used in the injector 1 preferably include powder (ZPP) containing zirconium and potassium perchlorate, powder (THPP) containing titanium hydride and potassium perchlorate, powder (TiPP) containing titanium and potassium perchlorate, powder (APP) containing aluminum and potassium perchlorate, powder (ABO) containing aluminum and bismuth oxide, powder (AMO) containing aluminum and molybdenum oxide, powder (ACO) containing aluminum and copper oxide, powder (AFO) containing aluminum and iron oxide, or powder formed by a combination of a plurality of kinds of powder among these kinds of powder. These kinds of powder show a characteristic that, although these kinds of powder generate high-temperature and high-pressure plasma during combustion immediately after ignition, when temperature changes to the normal temperature and the combustion product condenses, generated pressure suddenly drops because these kinds of powder do not include a gas component. Powder other than these kinds of powder may be used as the ignition charge as long as appropriate injection is possible.

In the combustion chamber 6 shown in FIG. 5, an additional explosive component is not particularly disposed. However, in order to adjust transition of pressure applied to the injection solution via the piston 5, it is also possible to dispose, in the combustion chamber 6, a gas generating agent or the like that is burnt by the combustion product generated by the combustion of the ignition charge 22 and generates gas. Examples of the gas generating agent include single-base smokeless powder including 98 mass % of cellulose nitrate, 0.8 mass % of diphenylamine, and 1.2 mass % of potassium nitrate. It is also possible to use various gas generating agents used in a gas generator for an airbag and a gas generator for a seatbelt pretensioner. By adjusting the dimension, the size, and the shape, in particular, the surface shape of the gas generating agent disposed in the combustion chamber 6, it is possible to change a combustion completion time of the gas generating agent. Consequently, it is possible to adjust the transition of the pressure applied to the injection solution to desired transition, that is, transition in which the injection solution can appropriately reach the injection target region.

In the housing 2, a through-hole 7 having a fixed diameter along the axial direction thereof is provided. One end of the through-hole 7 communicates with the combustion chamber 6. The remaining one end reaches a housing space 2b side for housing the syringe 3. In the through-hole 7, the piston 5 made of metal is disposed to be capable of being propelled along the axial direction in the through-hole 7. One end of the piston 5 faces the combustion chamber 6 side. The remaining other end faces the housing space 2b side.

Figure 3:
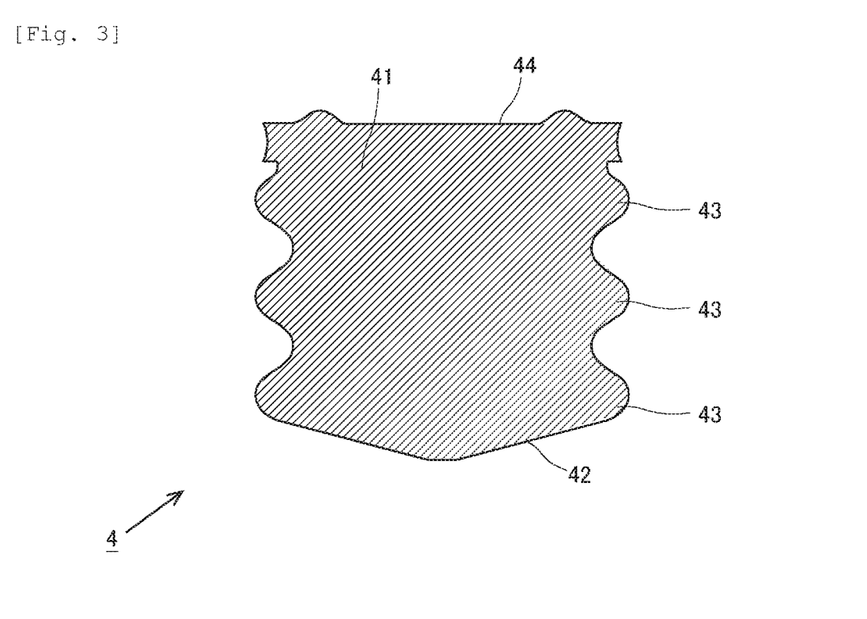
FIG. 3 is a diagram showing the configuration of a plunger, which is one of components of a syringe included in the injector shown in FIG. 1.
Figure 4:
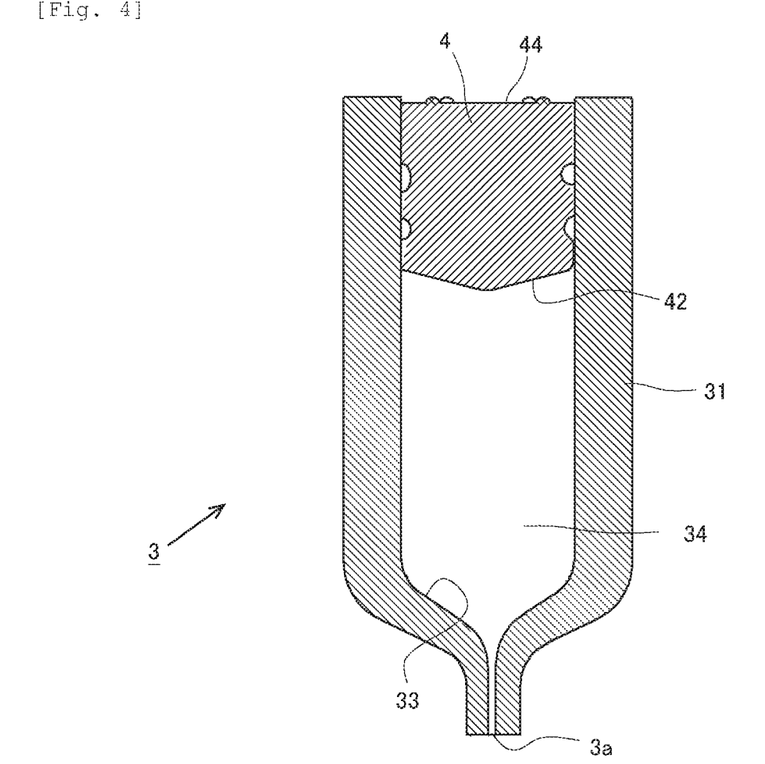
FIG. 4 is a diagram showing the configuration of the syringe included in the injector shown in FIG. 1.

The syringe 3, in which the injection solution is encapsulated, is explained with reference to FIG. 3 and FIG. 4. In FIG. 4, the schematic configuration of the syringe 3 is shown as a sectional view thereof. In FIG. 3, the schematic configuration of a plunger 4, which is one of components configuring the syringe 3, is shown as a sectional view thereof. The plunger 4 is formed of resin. As the material of the plunger 4, for example, butyl rubber and silicon rubber can be adopted. Further, examples of the material include styrene-based elastomer, hydrogenated styrene-based elastomer, and the styrene-based elastomer and the hydrogenated styrene-based elastomer added with polyethylene, polypropylene, polybutene, polyolefin such as α-olefin copolymer, liquid paraffin, oil such as process oil, and powder inorganic matters such as talc, cast, and mica. Further, polyvinyl chloride-based elastomer, olefin-based elastomer, polyester-based elastomer, polyamide-based elastomer, and polyurethane-based elastomer, various rubber materials (in particular, those subjected to vulcanization) such as natural rubber, isoprene rubber, chloroprene rubber, nitrile-butadiene rubber, and styrene-butadiene rubber, mixtures of the kinds of elastomer and the kinds of rubber, and the like can be adopted as the material of the plunger.

A body section 41 of the plunger 4 has a generally columnar shape. A plurality of annular protrusion sections 43 are formed in the outer circumference of the body section 41. In an example shown in FIG. 3, three annular protrusion sections 43 are formed. As shown in FIG. 4, the plunger 4 configured in this way is inserted into a hollow portion of the syringe main body 31 such that a rear end face 44 of the plunger 4 is generally flush with an end portion of the syringe main body 31 made of metal. The hollow portion is provided taking into account the size and the shape of the plunger 4 such that the plunger 4 can be inserted into the hollow portion with a distal end portion 42 at the head and the plunger 4 is capable of being propelled in the hollow portion in order to eject the injection solution. Note that the plurality of annular protrusion sections 43 provided in the outer circumference of the plunger 4 are elastically deformed when being inserted into the hollow portion because the annular protrusion sections 43 are made of resin. The adhesion of the plunger 4 and the syringe main body 31 can be improved. In particular, since the plurality of protrusion sections are provided, it is possible to suppress the pressurized injection solution from leaking out from between the plunger 4 and the syringe main body 31 during injection.

Since the plunger 4 is inserted into the syringe main body 31 in this way, a sealed space 34 for encapsulating the injection solution is formed in the syringe main body 31. A nozzle 3a for ejecting the injection solution to the outside is formed at the distal end portion of the syringe main body 31, that is, an end portion on the opposite side of an end portion into which the plunger 4 is inserted. The distal end portion 42 of the plunger 4 is formed in a shape for supplementing the shape of an outflow port 33 (see FIG. 4) extending to the nozzle 3a of the sealed space 34. That is, the shape of the outer surface of the distal end portion 42 and the shape of the outflow port 33 are generally coinciding shapes. Therefore, when the ejection of the injection solution is completed, it is possible to reduce an amount of the injection solution left in the sealed space 34 as much as possible.

The syringe unit 10 is configured by the housing 2 and the syringe 3 configured as explained above. The housing 2 is in a state in which the initiator 20 and the piston 5 are incorporated therein. However, the syringe 3, in which the injection solution is encapsulated, is not incorporated in the housing 2 itself. The user of the injector 1 can select an appropriate syringe 3 according to an injection purpose and install the syringe 3 in the housing space 2b of the housing 2. For example, the user can select the syringe 3 corresponding to a type and an amount of the injection solution that should be delivered to the injection target region and the syringe 3 including the nozzle 3a having a shape corresponding to characteristics (depth, resistance of the region, etc.) of the injection target region.

As shown in FIG. 1, the syringe 3 selected by the user is installed in the housing space 2b from the opening section provided in the side surface of the housing 2. At this point, the nozzle 3a located at the distal end portion of the syringe 3 is fit in a through-hole 9 provided in a distal end face 8 of the housing 2. Fixing in the housing space 2b is performed in a state in which a proximal end portion (an end portion on the opposite side of the distal end portion at which the nozzle 3a is provided) of the syringe 3 is pressed against the piston 5 side by fixing means by a not-shown elastic member. As a result, the syringe 3 is stably fixed in a state in which the syringe 3 is positioned by the through-hole 9 in the housing space 2b. In the fixed state, the rear end face 44 of the plunger 4 is opposed to the end face of the piston 5 already incorporated in the housing 2.

Note that, in the opening section for reaching the housing space 2b of the housing 2, a door section 2a for opening and closing the opening section is provided. When installing the syringe 3 in the housing 2 in the use of the injector 1, the user can access the opening section by opening the door section 2a. When installing the syringe 3 is completed, by closing the door section 2a, the user can suppress the syringe 3 from suddenly coming off.

As shown in FIG. 5, the conductive pins 28 of the initiator 20 incorporated in the housing 2 extend to the outside of the housing 2. The activating unit 30 is attached to the conductive pins 28. Consequently, the injector 1 is completed. A not-shown battery in the inside of the activating unit 30 and an activating switch 31 are provided for the activating unit 30. When the activating unit 30 is connected to the syringe unit 10 via the conductive pins 28, electric power can be supplied to the initiator 20 from the battery. The user pushes the activating switch 31, whereby electric power is actually supplied and the initiator 20 operates. In this way, the activating unit 30 functions as a power source of the injector 1. However, the activating unit 30 also functions as a grip portion for the user to grip the injector 1 during the use of the injector 1. The activating unit 30 itself is gripped by the user and supplies electric power. Therefore, the activating unit 30 is not a component contaminated by the user of the injector 1. Therefore, the activating unit 30 can be repeatedly used as long as the electric power of the battery lasts out.

When the initiator 20 operates, combustion gas is generated and the pressure of the combustion chamber 6 rises, whereby the piston 5 is propelled in the through-hole 7. Therefore, the plunger 4 is pushed and ejection of the injection solution is performed. At this point, according to the operation of the initiator 20, high-temperature combustion gas is generated. Therefore, it is likely that the resin material forming the housing 2 is thermally damaged. Therefore, in the housing 2, heat resistant members 11 are disposed in places where relatively large heat is likely to be transmitted to the resin material of the housing 2 from the initiator 20. Specifically, the heat resistant members 11 are disposed between the initiator 20 and the resin material and between the piston 5 and the resin material in a region reaching from the vicinity of the charge holder 23 of the initiator 20 to the periphery of the piston 5. The heat resistant members 11 can be formed of materials such as metal and ceramic.

Note that the heat resistant members 11 are also materials having high strength compared with the resin material of the housing 2. Therefore, as shown in FIG. 5, the heat resistant members 11 further extend to the vicinity of the housing space 2b in a position between the syringe 3 and the resin material of the housing 2 and also function as reinforcing members to reinforce the syringe 3 from the periphery thereof. As explained above, pressure is applied to the injection solution in the syringe 3 by the pressure of the combustion gas in the initiator 20, whereby the ejection of the injection solution is performed. At this point, a relatively large force is applied to the syringe main body 31 of the syringe 3 because, for example, the diameter of the nozzle 3 is small. Therefore, by surrounding the syringe main body 31 with the heat resistant members (the reinforcing members) 11, it is possible to avoid deformation and breakage of the syringe 3 during the ejection.

Note that, in this embodiment, the heat resistant members (the reinforcing members) 11 are continuously laid from the initiator 20 to the housing space 2b. However, the heat resistant members (the reinforcing members) 11 may be partially laid in places corresponding to the respective members according to necessity. Alternatively, as the heat resistant members (the reinforcing members) 11, members separated for each of portions to be covered such as the initiator 20 and the piston 5 may be used in combination. As the material of the heat resistant member 11 laid in the vicinities of the initiator 20 and the piston 5 and the material of the reinforcing member 11 laid in the vicinity of the housing space 2b, different materials may be respectively used according to required functions, that is, a heat insulating function and a reinforcing function.

To use the injector 1 configured as explained above, when the user uses the injector 1, the syringe 3 selected according to an injection purpose is installed in the housing 2, in which the initiator 20 and the piston 5 are incorporated, and the activating unit 30 is connected to the syringe unit 10 via the conductive pins 28 to complete the injector 1. To eject the injection solution to a predetermined injection target region, the user depresses the activating switch 31 in a state in which the user grips the activating unit 30 and presses the nozzle 3a against the predetermined injection target region. Consequently, the initiator 20 operates and ejection of the injection solution is performed.

After completion of the injection, the user detaches the syringe unit 10 from the activating unit 30. On the other hand, the user discards the syringe unit 10 as it is without detaching the syringe 3 from the syringe unit 10. The activating unit 30 can be used for the next injection as long as electric power of the battery remains. As a result, even after the completion of the injection, since the syringe 3 is fixed on the inside of the syringe unit 10, the syringe unit 10 is considered to be in a state in which a residue generated from the initiator 20 less easily leaks out to the outside of the unit. Even if the injection solution leaks out from the syringe 3, since the syringe 3 stays on the inside of the syringe unit 10 and is replaced together with the syringe unit 10 in the next injection, it is possible to eliminate, as much as possible, likelihood that the hand of the user is contaminated by the leaked-out injection solution and the like.

Note that, in terms of sanitation and malfunction avoidance, before the use of the injector 1, the syringe 3 and the housing 2 are respectively desirably sealed and stored.

Modification 1

Figure 6:
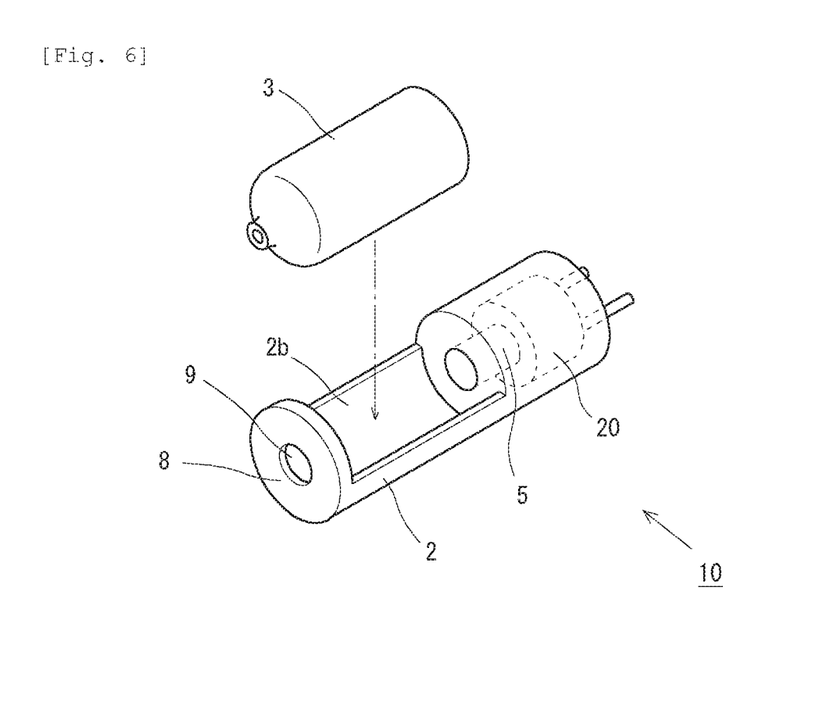
FIG. 6 is a second diagram showing the schematic configuration of the injector according to the present invention.

A first modification of the syringe unit 10 is explained with reference to FIG. 6. In the embodiment explained above, as shown in FIG. 1, the lid section 2a provided in the side surface of the housing 2 is opened and the syringe 3 is installed in the housing space 2b from the opening section. Instead of such a form, in the modification shown in FIG. 6, the lid section 2a is removed, approximately a half of the side surface of the housing 2 corresponding to the housing space 2b is cut off, and a relatively wide opening section is formed. Even in such a configuration, as explained above, the syringe 3 is installed in the housing space 2b in a state in which the proximal end face of the syringe 3 is pressed against the piston 5 side by the fixing means by the not-shown elastic member. Therefore, basically, the ejection of the injection solution is not affected. Since the lid section 2a is removed, the syringe is in a state in which the syringe is installed in a half-open space. However, after the completion of the injection, since the syringe is discarded together with the syringe unit, it is considered less likely that the hand of the user is contaminated.

Modification 2

Figure 7:
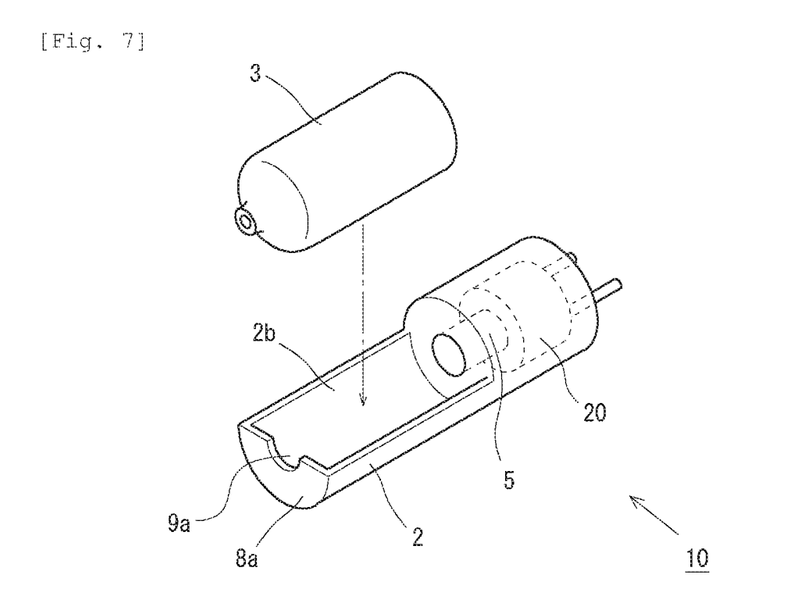
FIG. 7 is a third diagram showing the schematic configuration of the injector according to the present invention.

Further, a second modification of the syringe unit 10 is explained with reference to FIG. 7. A difference between the modification shown in FIG. 7 and the modification shown in FIG. 6 is the shapes of a distal end face of the housing 2 and a through-hole provided in the distal end face. In the modification shown in FIG. 7, a distal end face 8a of the housing 2 is formed in a shape cut of by approximately a half according to the shape of the housing space 2b. A through-hole 9a formed in the distal end face 8a is also formed in a generally semicircular shape. Even if the shapes of the distal end face 8a and the through-hole 9a are formed in this way, since the syringe 3 is pushed into the housing space 2b from above to be installed, positioning of the syringe 3 in the housing space 2b is not affected. Therefore, as in the embodiment explained above, the syringe 3 can be appropriately installed in the housing 2. After the completion of the injection, it is considered less likely that the hand of the user is contaminated.

Other Embodiments

With the injector 1 according to the present invention, other than injecting the injection solution into the skin structure, for example, in the field of regenerative medicine for a human, it is possible to seed a cultured cell, a stem cell, and the like in an injection target cell and a scaffold tissue/a scaffold. For example, as described in Japanese Patent Application Laid-Open No. 2008-206477, it is possible to inject, with the injector 1, a cell that those skilled in the art can determine as appropriate according to a region to be implanted and a purpose of recellularization, for example, an endothelial cell, an endothelia precursor cell, a bone marrow cell, a preosteoblast, a chondrocyte, a fibroblast, a skin cell, a muscle cell, a liver cell, a kidney cell, an intestinal cell, a stem cell, and all other cells considered in the field of regenerative medicine.

Further, the injector 1 according to the present invention can also be used for delivery of a DNA and the like to a cell, a scaffold tissue/a scaffold, and the like described in Japanese Translation of PCT Application No. 2007-525192. In this case, compared with delivering the DNA using a needle, it is considered more desirable to use the injector 1 according to the present invention because it is possible to suppress the influence on the cell, the scaffold tissue/the scaffold, and the like themselves.

Further, when directly delivering various genes, a cancer inhibition cell, a lipid envelope, and the like to a target cell or administering an antigen gene in order to improve immunity against pathogen, the injector 1 according to the present invention is also suitably used. Besides, the injector 1 can be used in the field of various disease treatments (the field described in Japanese Translation of PCT Application No. 2008-508881, Japanese Translation of PCT Application No. 2010-503616, and the like), the immunology field (the field described in Japanese Translation of PCT Application No. 2005-523679 and the like), and the like. Usable fields of the injector 1 are not intentionally limited.

REFERENCE SIGNS LIST

1 Injector
2 Housing
3 Syringe
4 Plunger
5 Piston
6 Combustion chamber
7 Through-hole
8, 8a Distal end face
9, 9a Through-holes
10 Syringe unit
20 Initiator
31 Syringe main body
34 Sealed space
41 Body section
42 Distal end portion
43 Annular protrusion section
44 Rear end face

What is claimed is:
1. A needleless injector comprising:
a syringe unit comprising a syringe that encapsulates an injection objective substance to be injected into an injection target region, an ignition device that provides energy for ejection to the injection objective substance encapsulated in the syringe by combustion of an explosive component, and a piston disposed between the syringe and the ignition device, said piston configured to transmit the energy provided by the ignition device to a syringe side; and
an activating unit configured to activate the ignition device in the syringe unit, wherein the syringe unit further comprises a housing, the housing including the ignition device and the piston, the housing further forming a housing space sized and shaped to accommodate the syringe, the housing further including an opening section in a side surface of the housing for installing the syringe into the housing space, wherein the syringe comprises a main body and a plunger, the main body forming an outflow port having a central nozzle at a distal end portion of the main body, the outflow port tapering towards the central nozzle to guide the injection objective substance to the central nozzle, the plunger being disposed in a proximal end portion of the main body on a side opposite to the distal end portion, the outflow port of the main body and the plunger forming at least a portion of a sealed space for encapsulating the injection objective substance prior to the injection objective substance being injected into the injection target region, the plunger being configured to be propelled by the energy transmitted by the piston and through the sealed space toward the central nozzle, when the syringe is installed in the housing the syringe is fixed so that the nozzle is exposed to the environment and the plunger of the syringe is disposed in a position opposed to the piston incorporated in the housing, wherein the housing further comprises a through-hole, wherein the through-hole connects an inside and an outside of the housing, in a distal end face, which is an end portion of the housing space, this end portion being on a side opposite to the ignition device, wherein the syringe is fixed to the housing in a state in which the syringe is held in the through-hole, and the nozzle is exposed to the environment via the through-hole when the syringe is installed in the housing, and wherein the main body including the outflow port and the central nozzle along with the plunger are together sized and shaped so as to be installable in and removable from the housing space through the opening section as a unitary structure.

2. The needleless injector according to claim 1, wherein the ignition device is integrated with the housing.

3. The needleless injector according to claim 2, wherein the housing is formed by injection molding of a resin material, and
the ignition device is integrated with the housing in a state in which the ignition device is embedded in the housing during the injection molding of the housing.

4. The needleless injector according to claim 3, wherein heat resistant members are provided between the ignition device and the resin material of the housing and between the piston and the resin material of the housing to cover at least parts of the ignition device and the piston disposed in the housing.

5. The needleless injector according to claim 3, wherein a reinforcing member is provided between the syringe and the resin material of the housing to cover at least a part of the syringe installed in the housing.

6. The needleless injector according to claim 1, wherein the housing further comprises a lid section configured to open and close.

7. The needleless injector according to claim 1, wherein the distal end portion of the syringe is narrowed in width to form the nozzle.

8. The needleless injector according to claim 7, wherein at least a portion of an outer circumference of the nozzle is not surrounded by the housing of the syringe unit.

9. The needleless injector according to claim 1, wherein a plurality of annular protrusions are provided on an outer circumference of the plunger.

10. The needleless injector according to claim 9, wherein the annular protrusions are configured to be elastically deformed when being inserted into the syringe.

11. The needleless injector according to claim 1, wherein the nozzle is an integral part of the syringe.

12. The needleless injector according to claim 1, wherein the through-hole is exposed to the environment.

13. The needleless injector according to claim 1, wherein the syringe has an inner surface and an outer surface, and wherein the distance between the inner surface and the outer surface of the syringe gradually changes at the distal end portion of the syringe.

* * * * *